US011096585B2

(12) United States Patent
Zhou et al.

(10) Patent No.: US 11,096,585 B2
(45) Date of Patent: Aug. 24, 2021

(54) NON-INVASIVE OPTICAL MEASUREMENT SYSTEM AND METHOD FOR NEURAL DECODING

(71) Applicant: HI LLC, Los Angeles, CA (US)

(72) Inventors: Haojiang Zhou, Los Angeles, CA (US); Roarke Horstmeyer, Durham, NC (US); Haowen Ruan, Los Angeles, CA (US); Yuecheng Shen, Guangzhou University (CN); Jamu Alford, Simi Valley, CA (US)

(73) Assignee: HI LLC, Los Angeles, CA (US)

( * ) Notice: Subject to any disclaimer, the term of this patent is extended or adjusted under 35 U.S.C. 154(b) by 316 days.

(21) Appl. No.: 16/385,265

(22) Filed: Apr. 16, 2019

(65) Prior Publication Data

US 2019/0336001 A1 Nov. 7, 2019

Related U.S. Application Data

(60) Provisional application No. 62/666,978, filed on May 4, 2018, provisional application No. 62/740,814, filed on Oct. 3, 2018.

(51) Int. Cl.
*A61B 5/00* (2006.01)
*A61B 5/24* (2021.01)
*A61B 5/026* (2006.01)

(52) U.S. Cl.
CPC .......... *A61B 5/0075* (2013.01); *A61B 5/0042* (2013.01); *A61B 5/0066* (2013.01);
(Continued)

(58) Field of Classification Search
CPC ....... A61B 5/24; A61B 5/0075; A61B 5/0042; A61B 5/0066
See application file for complete search history.

(56) References Cited

U.S. PATENT DOCUMENTS 5,528,365 A 6/1996 Gonatas
5,983,120 A 11/1999 Groner et al.
(Continued)

FOREIGN PATENT DOCUMENTS

EP 656536 7/2004
WO WO2015109005 7/2015
(Continued)

OTHER PUBLICATIONS

Erin M. Buckley et al., "Diffuse correlation spectroscopy for measurement of cerebral blood flow: future prospects," Neurophotonics, Apr. 15, 2019.
(Continued)

*Primary Examiner* — Joseph M Santos Rodriguez
(74) *Attorney, Agent, or Firm* — Michael J. Bolan; Vista IP Law Group, LLP

(57) ABSTRACT

A non-invasive optical measurement system comprises an optical source for generating source light, and an interferometer for splitting the source light into sample light and reference light, delivering the sample light into an anatomical structure, resulting in physiological-encoded signal light that exits the anatomical structure, and combining the signal light and the reference light into at least three phase-modulated interference light patterns. The optical path lengths of the respective source light and sample light match within a coherence length of the source light. The system further comprises at least three optical detectors configured for respectively detecting the interference light patterns, and a processor configured for determining a time-lapsed complex field of the signal light based on the interference light patterns, determining a decorrelation speed of the time-lapsed complex field of the signal light, and identifying a physiological event in the anatomical structure based on the determined decorrelation speed of the signal light.

30 Claims, 8 Drawing Sheets

(52) U.S. Cl.
CPC .............. *A61B 5/24* (2021.01); *A61B 5/0064* (2013.01); *A61B 5/0077* (2013.01); *A61B 5/0261* (2013.01); *A61B 5/4064* (2013.01); *A61B 2576/026* (2013.01)

(56) References Cited

U.S. PATENT DOCUMENTS

| | | | |
|---|---|---|---|
| 6,697,660 | B1 | 2/2004 | Robinson |
| 7,643,858 | B2 | 1/2010 | Agashe et al. |
| 8,082,015 | B2 | 12/2011 | Yodh et al. |
| 13,954,133 | | 2/2015 | Hanlon et al. |
| 9,157,858 | B2 | 10/2015 | Claps |
| 9,946,344 | B2 | 4/2018 | Ayaz et al. |
| 2010/0210952 | A1 | 8/2010 | Taira et al. |
| 2015/0182136 | A1 | 7/2015 | Durduran et al. |
| 2016/0345880 | A1 | 12/2016 | Nakaji et al. |
| 2018/0070831 | A1 | 3/2018 | Sutin et al. |
| 2018/0089531 | A1 | 3/2018 | Geva et al. |
| 2018/0103861 | A1 | 4/2018 | Sutin et al. |
| 2018/0185667 | A1 | 7/2018 | Huang |
| 2018/0306716 | A1 | 10/2018 | Ashrafi |

FOREIGN PATENT DOCUMENTS

| | | |
|---|---|---|
| WO | WO2016164900 | 10/2016 |
| WO | WO2017147539 | 8/2017 |
| WO | WO2018090040 | 5/2018 |

OTHER PUBLICATIONS

M. Pagliazzi et al., "Time domain diffuse correlation spectroscopy with a high coherence pulsed source: in vivo and phantom results," Biomedical Optics Express, vol. 8, No. 11, Nov. 1, 2017.

Turgut Durduran et al., "Diffuse correlation spectroscopy for non-invasive, micro-vascular cerebral blood flow measurement," NeuroImage, Jun. 6, 2013.

Marinko V. Sarunic, "Instantaneous complex conjugate resolved spectral domain and swept-source OCT using 3x3 fiber couplers," Optics Express, vol. 13, No. 3, Feb. 7, 2005.

Yu Shang, et al., "Diffuse Correlation Spectroscopy (DCS) for Assessment of Tissue Blood Flow in Skeletal Muscle: Recent Progress," Anat Physiol. Dec. 1, 2013.

Yu Shang, et al., "Clinical Applications of Near-infrared Diffuse Correlation Spectroscopy and Tomography for Tissue Blood Flow Monitoring and Imaging," Physiol Meas. Apr. 2017.

David A. Boas, "Establishing the diffuse correlation spectroscopy signal relationship with blood flow," Neurophotonics, Jul.-Sep. 2016.

David Huang, "Optical Coherence Tomography," http://science.sciencemag.org, May 10, 2018.

Jun Li, "Pulsation-resolved deep tissue dynamics measured with diffusing-wave spectroscopy," Optics Express, vol. 14, No. 17, Aug. 21, 2006.

Chao Zhou, et al., "Diffuse optical correlation tomography of cerebral blood flow during cortical spreading depression in rat brain," vol. 14, No. 3, Optics Express, Feb. 6, 2006.

Detian Wang, "Fast blood flow monitoring in deep tissues with real-time software correlators," Biomedical Optics Express, vol. 7, No. 3, Mar. 1, 2016.

G. Dietsche, et al."Fiber-based multispeckle detection for time-resolved diffusing-wave spectroscopy: characterization and application to blood flow detection in deep tissue," Applied Optics 46, 35, pp. 8506-8514, Apr. 18, 2007.

D.A. Boas, et al. "Scattering and Imaging with Diffusing Temporal Field Correlations," Physical Review Letters, vol. 75, No. 9, Aug. 28, 1995.

Micro Photon Devices, "Single Photon Counting Camera," SPC3 User Manual Version 1.1.0—Nov. 2015.

Katarzyna Zarychta, et al., "Time-resolved diffusing wave spectroscopy with a CCD camera," Optics Express, vol. 18, No. 16, Aug. 2, 2010.

Jason Sutin, et al., "Time-domain diffuse correlation spectroscopy," Optica, vol. 3, No. 9, Sep. 2016.

Benedict Hebert, et al., "Spatiotemporal Image Correlation Spectroscopy (STICS) Theory, Verification, and Application to Protein Velocity Mapping in Living CHO Cells," Biophysical Journal, vol. 88, May 2005.

NON-INVASIVE OPTICAL MEASUREMENT SYSTEM AND METHOD FOR NEURAL DECODING

RELATED APPLICATION DATA

Pursuant to 35 U.S.C. § 119(e), this application claims the benefit of U.S. Provisional Patent Application 62/666,978, filed May 4, 2018, and U.S. Provisional Patent Application 62/740,814, filed Oct. 3, 2018, which are expressly incorporated herein by reference.

FIELD OF THE INVENTION

The present inventions relate to methods and systems for non-invasive measurements in the human body, and in particular, methods and systems related to detecting physiologically-dependent optical parameters in the human body, e.g., the brain.

BACKGROUND OF THE INVENTION

Measuring neural activity in the brain is useful for medical diagnostics, neuromodulation therapies, neuroengineering, or brain-computer interfacing.

Conventional methods for measuring neural activity in the brain include diffusive optical imaging techniques, which employ moderate amounts of near-infrared or visible light radiation, thus being comparatively safe and gentle for a biological subject in comparison to X-Ray Computed Tomography (CT) scans, positron emission tomography (PET), or other methods that use higher-energy and potentially harmful ionizing radiation. Moreover, in contrast to other known methods, such as functional magnetic resonance imaging (fMRI), these optically-based imaging methods do not require large magnets or magnetic shielding, and thus, can be scaled to wearable or portable form factors, which is especially important in applications, such as brain-computer interfacing.

However, because optical imaging techniques rely on light, which scatters many times inside brain, skull, dura, pia, and skin tissues, the light paths occurring in these techniques comprise random or "diffusive" walks, and therefore, only limited spatial resolution can be obtained by a conventional optical detector, often on the order of centimeters, with usable penetration depths being limited to a few millimeters. The reason for this limited spatial resolution is that the paths of photons striking the detector in such schemes are highly variable and difficult, and even impossible, to predict without detailed microscopic knowledge of the scattering characteristics of the brain volume of interest, which is typically unavailable in practice (i.e., in the setting of non-invasive measurements through skull for detecting neural activity in the brain for brain-computer interfacing). In summary, light scattering has presented challenges for optical detection techniques in achieving high spatial resolution inside tissue regions at depths below a user's skull, e.g., multiple centimeters. Moreover, the diffusive nature of light propagation also creates challenges for measurements of fast changes in optical scattering inside tissue, since essentially all paths between source and detector are highly scattered to begin with.

One commercially available non-invasive imaging method, referred to as optical coherence tomography (OCT), is capable of acquiring images with high z-resolution (depth), but at relatively shallow depths (1 mm-2 mm). Traditional OCT systems use coherent light (typically light in the near-infrared spectrum) to capture sub-surface images within optical scattering media (such as biological tissue) at a micrometer-resolution. The OCT system directs an optical beam at biological tissue and collects a small portion of the light that reflects from sub-surface features of the biological tissue. Although most of the light directed at the biological tissue is not reflected, but rather, diffusively scatters and contributes to background that may obscure the image, traditional OCT utilizes a holographic (or interferometric) technique to select, via optical path selection, the photons that directly reflect off of the sub-surface features (i.e., the ballistic backscattered photons), and reject photons that scatter multiple times in the biological tissue before detection.

In particular, in a traditional OCT system, light from a light source is split into two paths along two different arms of an interferometer: a reference arm and a sample arm. In the sample arm, sample light is backscattered through a sample medium, and in the reference arm, reference light is back-reflected by a mirror where it recombines with the backscattered sample light at a coupler. Interference light is formed by any sample light that has an optical path length that matches, within the coherence length of the optical source, the optical path length traveled by the reference light. The intensity of the backscattering sample light having that optical path length can then be detected within the interference light.

Previous commercial OCT systems acquired data in the time domain (TD-OCT), and coherence gated the backscattered light from various depths in the biological tissue by adjusting the position of the mirror to tune the optical path length of the reference, such that only sample light having the matching optical path length is selected for detection at any given time. Current commercial OCT systems acquire data in the Fourier domain (FD-OCT), and do not involve adjusting the delay of the reference arm, and thus do not coherence gate, but rather involve acquiring an interferometric signal as a function of optical wavelength by combining the sample light and the reference light from a source with a finite spectral width at a fixed reference arm delay, and then Fourier-transforming the spectral or frequency-resolved interference as a function of photon time-of-flight to obtain the various depths in the biological tissue. It has been shown that FD-OCT has a significantly greater signal-to-noise (SNR) than TD-OCT (see Michael A. Choma, et al., "*Sensitivity Advantage of Swept Source and Fourier Domain Optical Coherence Tomography*," Optics Express, Vol. 11, No. 18, 8 Sep. 2003). Two distinct methods have been developed that employ the FD approach: (1) swept-source (SS-OCT), which time-encodes optical wavelengths by rapidly tuning a narrowband source through a broad optical bandwidth; and 2) spectral domain (SD-OCT), which uses a broadband light source to achieve spectral discrimination.

Regardless of the type, the depth at which a traditional OCT system images biological tissue is limited, because at greater depths the proportion of light that escapes without scattering (i.e., the ballistic light) is too small to be detected. Thus, the clinical applications of a traditional OCT system have, thus far, been limited to imaging sub-surface features, such as obtaining high-resolution ophthalmic images of the retina. As such, traditional OCT systems are presently insufficient for measuring neural activity in the regions of the brain at deeper depths (i.e., deeper than 2 mm).

Another type of diffusive optical imaging technique, referred to as interferometric Near-Infrared Spectroscopy (iNIRS) (see Borycki, Dawid, et al., "*Interferometric Near-Infrared Spectroscopy (iNIRS) for Determination of Optical* and *Dynamical Properties of Turbid Media*," Optics Express, Vol. 24, No. 1, Jan. 11, 2016), has been developed. While traditional OCT utilizes low-coherence interferometry to produce cross-sectional images of biological specimens with a resolution of few micrometers and an imaging range of 1-2 mm, the goal of iNIRS is to use high coherence interferometry to measure optical and dynamical properties of thick scattering media at a depth on the order of a few centimeters, at the cost of reduced axial resolution.

As discussed in Borycki, iNIRS can be implemented in a time domain approach, referred to as TD NIRS, or a frequency domain approach, referred to as FD NIRS. In TD NIRS, a near-infrared picosecond light pulse is delivered into tissue, and the reflected optical intensity is detected and analyzed as a function of time. In particular, the optical properties (e.g., absorption and scattering coefficients) of the tissue can be determined from the temporal features, such as slope and the peak location, of the photon distribution of time-of-flight (DTOF) of the resulting temporal signal. However, conventional TD NIRS systems require expensive pulsed lasers and complex time-correlated single photon counting detection, making widespread adoption of this technology challenging. Furthermore, typical TD NIRS systems are somewhat complicated in that they must record the arrival time of photons over the relevant time period in order to acquire the full DTOF, and furthermore, must operate at high enough speeds to record this full DTOF at a high enough resolution to extract the relevant signal. In FD NIRS, sinusoidally modulated light is delivered into tissue. The optical properties of the tissue are determined from the amplitude attenuation and phase shift of the reflected optical light. However, FD NIRS typically does not directly resolve the DTOF, and the modulation/demodulation schemes can be complex and expensive. One embodiment of the FD NIRS system disclosed in Borycki utilizes a frequency-swept laser with an instantaneous linewidth and tuning range narrower by several orders of magnitude than in typical OCT systems, enabling the measurement of longer photon path lengths (up to tens of centimeters) at the cost of reduced axial resolution. However, such fast-sweeping laser source is relatively expensive and is subject to instability due to changes in temperature, thereby compromising its signal-to-noise ratio (SNR).

Furthermore, the iNIRS systems described above have not been demonstrated to measure fast-optical signals, which refers to changes in optical scattering that occur when light propagating through active neural tissue (e.g., active brain tissue) is perturbed through a variety of mechanisms, including, but not limited to, cell swelling, cell volume change, changes in membrane potential, changes in membrane geometry, ion redistribution, birefringence changes, etc. (see Hill D. K. and Keynes, R. D., "Opacity Changes in Stimulated Nerve," J. Physiol., Vol. 108, pp. 278-281 (1949); Foust A. J. and Rector D. M., "Optically Teasing Apart Neural Swelling and Depolarization," Neuroscience, Vol. 145, pp. 887-899 (2007)). Because fast-optical signals are associated with neuronal activity, rather than hemodynamic responses, fast-optical signals may be used to detect brain activity with relatively high temporal resolution.

As discussed in Gratton G., Fabiani M, "Fast-optical Imaging of Human Brain Function," Vol. 4, Article 52, pp. 1-9 (June 2010)), the basic assumption for detecting naturally occurring fast-optical signals is that fast-optical signals change the path length distribution of light propagating through a sample. The mechanisms of fast-optical signals alter the amount or directionality distribution of local scattering, thereby scattering light towards deeper or shallower depths, resulting in more or less time spent in the tissue or other changes in the fraction of photons traveling on deep versus shallower paths through tissue, or more generally longer or shorter paths through tissue. Thus, fast-optical signals give rise to or are correlated with a change in average optical path length between source and for diffusive light propagating through the sample.

Gratton concludes that phase delay measurements are particularly interesting for detecting fast-optical signals associated with changing light scattering inside the brain since, compared to light intensity measurements (as performed by the FD NIRS technique), since phase delay measurements have a greater sensitivity for deeper locations due to the fact that photons traveling a very long path have a greater influence on the mean value of phase delay; phase delay measurements have a greater spatial resolution due to the large effect on the phase value in response to even small changes in the relative number of photons traveling long or short paths (5-10 mm for phase delay measurement compared to 10-20 mm for intensity measurements); and phase delay measurements are largely insensitive to variations in the total amount of light injected into the tissue or measured by the detector, since such variations will equally influence photons traveling long and shorter paths, and therefore have no net effect on the phase delay parameter, and thus are largely insensitive to movements.

However, fast-optical signals are very small (on the order of $\frac{1}{1000}$ for intensity measurements and picoseconds or fractions thereof for phase delay measurement), and thus, there is a challenge separating fast-optical signals from background noise. Gratton has proposed reducing the background noise by using signal averaging over a large number of trials. The disadvantage of this is, of course, the requirement that multiple measurements would need to be taken to detect a fast-optical signal, limiting applicability for "real time" applications, e.g., brain-computer interfacing.

Another emerging technique referred to as Diffuse Correlation Spectroscopy (DCS) applies continuous measurement of relative blood flow in tissue using near-infrared light at the cost of reduced axial resolution much like the iNIRS systems described above. Specifically, DCS techniques irradiate tissue regions with a source of light that diffuses through the medium, and then measure the temporal intensity fluctuations of photon streams that have been scattered within the tissue. The tissue's properties, for example blood flow rate, are then determined by performing a temporal autocorrelation function of the diffused light. Also, like the iNIRS systems described above, the DCS techniques have not been demonstrated to measure fast-optical signals. It is believed the signal-to-noise (SNR) of DCS measurements, and thus the temporal sensitivity of DCS techniques to fast-optical signals, may be too low to enable effective measurement of fast-optical signals.

There, thus, remains a need to provide a simpler and less expensive optical measurement system with an improved temporal sensitivity to fast-optical signals.

SUMMARY OF THE INVENTION

In accordance with a first aspect of the present inventions, a non-invasive optical measurement system comprises an optical source (e.g., a continuous wave (CW) optical source) configured for generating source light during a measurement period. The measurement period can be, e.g., at least 50 µs, or even at least 100 µs. The non-invasive optical measurement system further comprises an interferometer configured for splitting the source light into sample light and reference light, delivering the sample light into an anatomical structure (e.g., a brain), such that the sample light is scattered by the anatomical structure, resulting in physiological-encoded signal light that exits the anatomical structure, and combining the physiological-encoded signal light and the reference light into at least three phase-modulated interference light patterns (e.g., ninety degrees out of phase). The optical path lengths of the respective source light and sample light match within a coherence length of the source light. The coherence length of the optical source may, e.g., be equal to or less than 1 cm. The non-invasive optical measurement system further comprises at least three optical detectors configured for respectively detecting the phase-modulated interference light patterns over the measurement period.

In one embodiment, the interferometer comprises a beam splitter configured for splitting the source light into the sample light and the reference light, and an optical beam combiner configured for combining the physiological-encoded signal light and the reference light into the phase-modulated interference light patterns. The optical beam combiner may comprise a first input port configured for receiving the physiological-encoded signal light, a second input port configured for receiving the reference light, a first output port configured for outputting a first one of the phase-modulated interference light patterns to a first one of the optical detectors, a second output port configured for outputting a second one of the phase-modulated interference light patterns to a second one of the optical detectors, and a third output port configured for outputting a third one of the phase-modulated interference light patterns to a third one of the optical detectors.

The non-invasive optical measurement system further comprises a processor configured for determining a time-lapsed complex field of the physiological-encoded signal light over the measurement period based on the detected phase-modulated interference light patterns, determining a decorrelation speed of the time-lapsed complex field of the physiological-encoded signal light, and identifying a physiological event (e.g., one that is indicative of neural activity, such as, e.g., a fast-optical signal) in the anatomical structure based on the determined decorrelation speed of the physiological-encoded signal light. In one embodiment, the processor is configured for determining the decorrelation speed of the time-lapsed complex field of the physiological-encoded signal light by performing an autocorrelation function of the time-lapsed complex field of the physiological-encoded signal light. The processor may be configured for performing the autocorrelation function of the time-lapsed complex field of the physiological-encoded signal light by computing a Fourier transform of the time-lapsed complex field of the physiological-encoded signal light, squaring an amplitude of the Fourier transform of the time-lapsed complex field of the physiological-encoded signal light, and computing an inverse Fourier transform of the squared amplitude of the Fourier transform of the time-lapsed complex field of the physiological-encoded signal light. The processor may be configured for identifying the physiological event in the anatomical structure, at least partially, by comparing the determined decorrelation speed of the physiological-encoded signal light to a reference decorrelation speed.

In an optional embodiment, the processor is configured for determining a time-lapsed absolute intensity of the physiological-encoded signal light over the measurement period based on the detected phase-modulated interference light patterns, computing a moving average of the time-lapsed absolute intensity of the physiological-encoded signal light over the measurement period, and identifying another physiological event (e.g., a hemodynamic change) in the anatomical structure based on the computed moving average of the time-lapsed absolute intensity of the physiological-encoded signal light over the measurement period.

In accordance with a second aspect of the present inventions, a non-invasive optical measurement method comprises generating source light (e.g., continuous wave (CW) source light) during a measurement period. The measurement period can be, e.g., at least 50 µs, or even at least 100 µs. The non-invasive optical measurement method further comprises splitting the source light into sample light and reference light, delivering the sample light into an anatomical structure (e.g., a brain), such that the sample light is scattered by the anatomical structure, resulting in physiological-encoded signal light that exits the anatomical structure, and combining the physiological-encoded signal light and the reference light into at least three phase-modulated interference light patterns (e.g., ninety degrees out of phase). The optical path lengths of the respective source light and sample light match within a coherence length of the source light. The coherence length of the source light may, e.g., be equal to or less than 1 cm. The non-invasive optical measurement method further comprises respectively detecting the phase-modulated interference light patterns over the measurement period.

The non-invasive optical measurement method further comprises determining a time-lapsed complex field of the physiological-encoded signal light over the measurement period based on the detected phase-modulated interference light patterns, determining a decorrelation speed of the time-lapsed complex field of the physiological-encoded signal light, and identifying a physiological event (e.g., one that is indicative of neural activity, such as, e.g., a fast-optical signal) in the anatomical structure based on the determined decorrelation speed of the physiological-encoded signal light. In one optical measurement method, the decorrelation speed of the time-lapsed complex field of the physiological-encoded signal light is determined by performing an autocorrelation function of the time-lapsed complex field of the physiological-encoded signal light. For example, the autocorrelation function of the time-lapsed complex field of the physiological-encoded signal light may be performed by computing an amplitude of a Fourier transform of the time-lapsed complex field of the physiological-encoded signal light, squaring the amplitude of the Fourier transform of the time-lapsed complex field of the physiological-encoded signal light, and computing an inverse Fourier transform of the squared amplitude of the Fourier transform of the time-lapsed complex field of the physiological-encoded signal light. The physiological event in the anatomical structure may be identified, at least partially, by comparing the determined decorrelation speed of the physiological-encoded signal light to a reference decorrelation speed.

A non-invasive optical measurement method further comprises determining a time-lapsed absolute intensity of the physiological-encoded signal light over the measurement period based on the detected phase-modulated interference light patterns, computing a moving average of the time-lapsed absolute intensity of the physiological-encoded signal light over the measurement period, and identifying another physiological event (e.g., a hemodynamic change) in the anatomical structure based on the computed moving average of the time-lapsed absolute intensity of the physiological-encoded signal light over the measurement period.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings.

Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
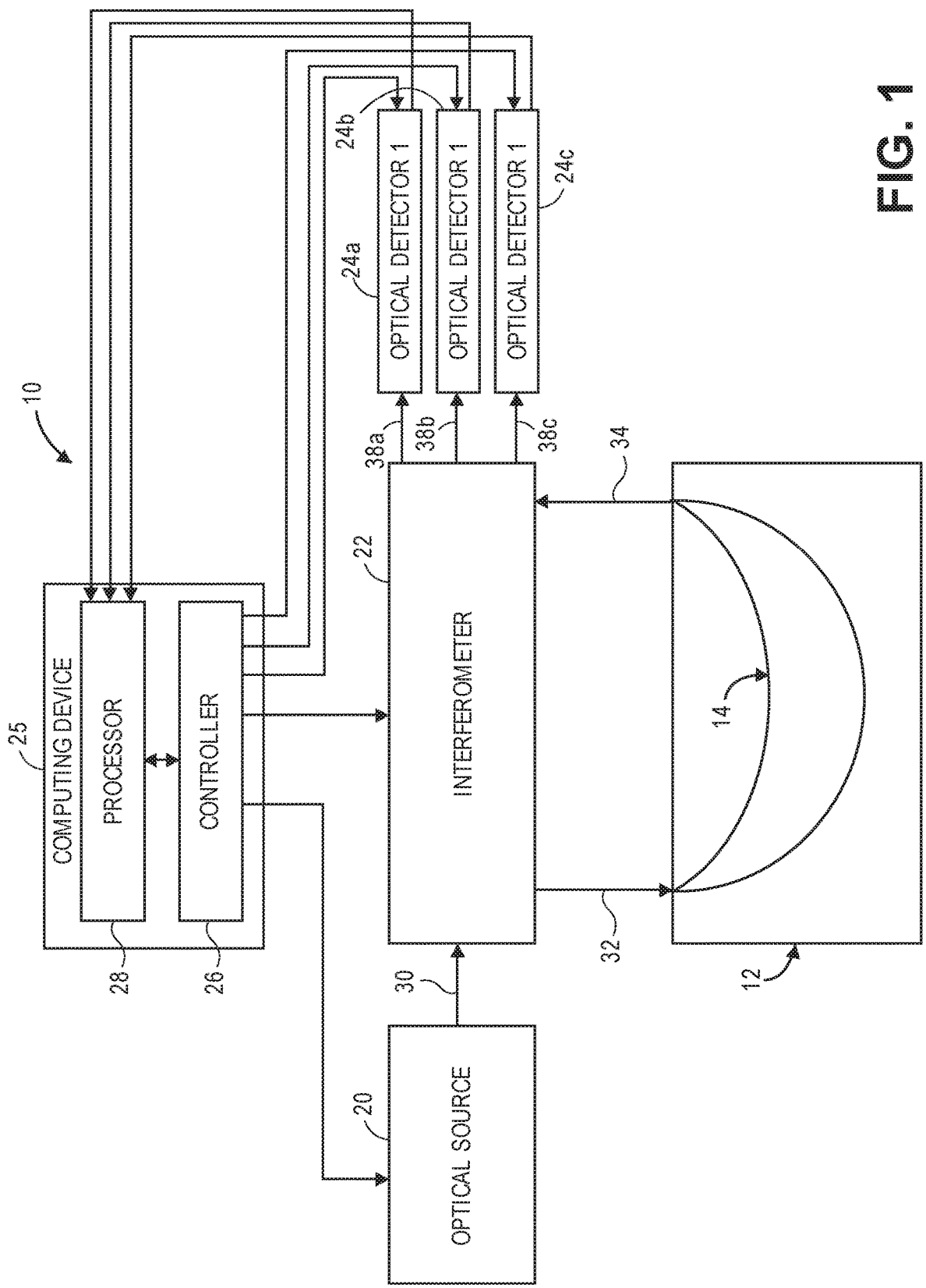
FIG. 1 is a block diagram of an optical measurement system constructed in accordance with one embodiment of the present inventions.

Referring now to FIG. 1, a generalized embodiment of an optical measurement system 10 constructed in accordance with the present inventions will be described. The optical measurement system 10 is a holographic optical system (i.e., a system that mixes detected signal light against reference light in order to increase the signal-to-noise ratio (SNR) of the relevant signal). As such, the optical measurement system 10 focuses on the measurement of multiple-scattered signal light of a depth-correlated optical path length, and is capable of detecting physiological events in tissue at a penetration depth of multiple centimeters, as opposed to ballistic signal light measured by a traditional Optical Coherence Tomography (OCT) system.

The optical measurement system 10 utilizes a simple and relatively inexpensive, low coherence, continuous wave (CW) source, in contrast to the pulsed laser or swept laser respectively required by TD-NIRS and FD-NIRS systems (see Background section). Furthermore, the optical measurement system 10 coherence gates the signal light, and therefore, does not require a complex detection scheme to measure the full photo distribution of time-of-flight (DTOF) of the signal light as required by conventional TD-NIRS systems, and does not require the complex modulation/demodulation schemes as required by conventional FD-NIRS systems. Furthermore, the optical measurement 10 has an increased signal-to-noise (SNR) due to coherence gating, allowing the optical measurement system 10 to be more sensitive to scattering changes caused by fast-optical signals, and can detect a fast-optical signal within one measurement period. Fast-optical signal refers to changes in optical scattering that occur when light propagating through active neural tissue (e.g., active brain tissue) is perturbed through a variety of mechanisms, including, but not limited to, cell swelling, cell volume change, changes in membrane potential, changes in membrane geometry, ion redistribution, birefringence changes, etc. Fast-optical signals are associated with neuronal activity, rather than hemodynamic responses, and fast-optical signals may be used to detect brain activity with relatively high temporal resolution.

The optical measurement system 10 is designed to non-invasively acquire physiological-encoded signal light (i.e., signal light representative of a physiologically-dependent optical parameter) in the anatomical structure 12, processing the physiological-encoded signal light, and determining the presence and depth of a physiological event in the anatomical structure 12 based on the processed physiological-encoded signal light. In the illustrated embodiment, the anatomical structure 12 is a brain, in which case, the optical measurement system 10 may identify the presence and location of neural activity within the brain 12. Although for exemplary purposes, the optical measurement system 10 is described as acquiring physiological-encoded data from brain tissue, variations of such optical measurement system 10 may be used to acquire physiological-encoded data from other anatomical structures of a human body, animal body and/or biological tissue.

In the illustrated embodiment, the physiological-encoded data acquired by the optical measurement system 10 is neural-encoded data, and the physiological event is a fast-optical signal, although in alternative embodiments, the physiological event may be a slower hemodynamic change, e.g., Doppler shift due to moving blood flow, changes in blood volume, metabolism variations such a blood oxygen changes. However, as will be described in further detail below, the optical measurement system 10, when properly tuned to a specific type of physiological event, is capable of decoding light propagating through the brain to detect any physiological event that causes a change in an optical property of the brain 12.

The neural activity information (or the acquired neural-encoded data from which it is derived) may be transmitted to external programmable devices for use (e.g., computed, processed, stored, etc.) therein, e.g., medical devices, entertainment devices, neuromodulation stimulation devices, lie detection devices, alarm systems, educational games, brain interface devices, vehicle's audio systems, vehicle's autonomous driving systems, etc., and/or may be used internally to adjust the detection parameters of the optical measurement system 10, such as increasing or decreasing the strength of the optical source and/or data compression and/or analysis, such a Fast Fourier Transform (FFT) and/or statistical analysis.

Although the optical measurement system 10, for purposes of brevity, is described herein as acquiring neural-encoded data from the brain 12 by using a single fixed source-detector arrangement to create one bundle of detected optical paths 14 through the brain 12 in a single measurement period, in an alternative implementation capable of localizing the fast-optical signal in an x-y plane along the surface of the brain 12, variations of the optical measurement system 10 may utilize more complex source-detector arrangements (e.g., single-source multi-detector, multi-source single-detector, or multi-source multi-detector) to simultaneously create multiple bundles of optical paths spatially separated from each other within the brain 12 in a single measurement period. In other embodiments, the optical measurement system 10 may utilize a movable source-detector arrangement to sequentially create multiple bundles of optical paths over several measurement periods, as described in U.S. Provisional Patent Application Ser. No. 62/692,074, entitled "Frequency Domain Optical Spectroscopy For Neural Decoding," U.S. patent application Ser. No. 16/379,090, entitled "Non-Invasive Frequency Domain Optical Spectroscopy For Neural Decoding," and U.S. Provisional Patent Application Ser. No. 62/692,124, entitled "Interferometric Frequency-Swept Source and Detector in a Photonic Integrated Circuit," which are expressly incorporated herein by reference. Thus, the optical detection system 10 may detect and localize physiological events associated with neural activity in the brain, including fast-optical signals, in three-dimensions, with two of the dimensions represented as an x-y plane spanning the surface of the brain 12 encoded within the spatially separated multiple sample paths and the third dimension (z-dimension or depth into the brain 12) being encoded within frequency components of photons propagating along the sample paths 14.

Referring still to FIG. 1, the optical measurement system 10 generally comprises an optical source 20, wherein various types of optical sources may be used as described below, an interferometer 22, three optical detectors 24a, 24b, and 24c, a computing device or other similar device 25, which all operate together to non-invasively detect the presence and depth of a fast-optical signal in the brain 12. In this embodiment, only a single source-detector arrangement is described, although as discussed above, the optical measurement system 10 may employ a variety of source-detector arrangements.

The computing device 25 comprises a controller 26, a processor 28, a memory (not shown), a display (not shown), and an input device (not shown). The computing device 25 can, e.g., be a computer, tablet, mobile device, or any other suitable device for processing information. The computing device 25 can be local to the user or can include components that are non-local to the user. For example, in at least some embodiments, the user may operate a terminal that is connected to a non-local computing device. In other embodiments, the memory can be non-local to the user. The computing device 25 can utilize any suitable processor 28, including one or more hardware processors that may be local to the user or non-local to the user or other components of the computing device 25. The processor 28 is configured to execute instructions provided to the processor 28, as described below.

Any suitable memory can be used for the computing device 25. The memory can be a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal. The term "modulated data signal" can include a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display can be any suitable display device, such as a monitor, screen, or the like, and can include a printer. In some embodiments, the display is optional. In some embodiments, the display may be integrated into a single unit with the computing device 25, such as a tablet, smart phone, or smart watch. The input device can be, for example, a keyboard, mouse, touch screen, track ball, joystick, voice recognition system, or any combination thereof, or the like.

Although the controller 26 and processor 28 are described herein as being separate components, it should be appreciated that portions or all functionality of the controller 26 and processor 28 may be performed by a single component. Furthermore, although all of the functionality of the controller 26 is described herein as being performed by a single component, and likewise all of the functionality of the processor 28 is described herein as being performed by a single component, such functionality each of the controller 26 and the processor 28 may be distributed amongst several computing devices. Moreover, it should be appreciated that those skilled in the art are familiar with the terms "controller" and "processor," and that they may be implemented in software, firmware, hardware, or any suitable combination thereof.

The optical source 20 is configured for generating source light 30. The optical source 20 may receive power from a drive circuit (not shown), which may include control inputs for receiving control signals from the controller 26 that cause the optical source 20 to emit the source light 30 at a selected time, duration, intensity, or coherence length. In one embodiment, the optical source 20 is a continuous wave (CW) optical source, although in alternative embodiments, the optical source 20 may be a pulsed wave (PW) optical source, in which case, the pulse width of the source light 30 can be at least as long as the measurement period.

The optical source 20 may take the form of a super luminescent diode (SLD), although other light sources, e.g., a distributed feedback (DFB) laser, a light emitting diode (LED), a diode-pumped solid-state (DPSS) laser, a laser diode (LD), a super luminescent light emitting diode (sLED), a titanium sapphire laser, and/or a micro light emitting diode (mLED), or similar laser to achieve an appropriate coherence length and extremely high amplitude stability, among other optical sources, may be used.

The optical source 20 may have either a predefined coherence length or a variable coherence length. Since the optical measurement system 10 is used to measure optical and dynamic properties at deeper depths in the brain tissue, as opposed to acquiring images of the brain tissue at a shallow depth, for example as acquired by traditional OCT systems, the optical source 20 preferably has an instantaneous spectral linewidth narrower by several orders of magnitude than in traditional TD-OCT systems, enabling the measurement of distinctly longer optical path lengths (of up to tens of centimeters) at the cost of reduced resolution (of the order of millimeters). To this end, the optical source 20 may be configured for generating source light 30 having a coherence length selected to correspond to the desired level of path-length selectivity (and thus, desired depth), e.g., from about 1 mm to about 1 cm, e.g., about 100-1000 µm for penetration depths of 6-10 mm below the surface of anatomical structure 12, and in the case illustrated below, the scalp, through the skull, and into the brain.

The source light 30 may be ultraviolet (UV) light, visible light, and/or near-infrared and infrared light, and may have any suitable wavelength, e.g., in the range of 350 nm-1800 nm. The source light 30 may be close to monochromatic in nature, comprising approximately a single-wavelength light, or the source light 30 may have a designated spectrum width (relative wide spectrum width compared to single-wavelength light) to achieve 1 mm or 1 cm coherence. As discussed in further detail below, the source light 30 has a narrow optical spectrum that is rapidly swept (e.g., changed over time) to functionally mimic or create an effective broad optical spectrum.

Notwithstanding the foregoing, it is preferred that the optical wavelength of the source light 30 be selected to maximize sensitivity to the specific physiological event of interest. For example, in the preferred case where the physiological event of interest is the presence of a fast-optical signal, an optical wavelength greater than hemoglobin absorption wavelengths (e.g., greater than 850 nm) may be used for the source light 30 to detect scattering changes by materials other than blood, and/or to detect scattering by blood outside of wavelengths that are strongly absorbed by blood. Optionally, an optical wavelength equal to or greater than 1000 nm may be used for the source light 30 to maximize penetration within the target site, e.g., within the brain 12. In the additional or alternative case where the physiological event of interest is a hemodynamic change, an optical wavelength in the range of 550 nm to 850 nm may be used for the source light 30. Multiple optical wavelengths can be used for the source light 30 to allow different physiological events to be distinguished from each other. For example, source light 30 having two optical wavelengths of 900 nm and 700 nm can be respectively used to resolve fast-optical signals and hemodynamic changes. Alternatively, the wavelength of the source light 30 can be selected to maximize the detector sensitivity.

The interferometer 22 is configured for splitting the source light 30 from the optical source 20 into sample light 32, which is delivered to the brain 12 along the bundle of optical paths 14 of a sample arm and exits the brain 12 as physiological-encoded (in this case, neural-encoded) signal light 34, and reference light 36 (shown in FIG. 2), which propagates along a reference arm outside of the brain 12. The interferometer 22 is further configured for combining the neural-encoded signal light 34 and the reference light 36 into three phase modulated interference light patterns 38a, 38b, 38c having one speckle (i.e., one optical mode that spatially has identical intensity and phase) interfering at a different phase with the reference light 36. In the preferred embodiment, the three phase modulated interference light patterns 38a, 38b, 38c differ from each other by ninety degrees (e.g., 0, $\pi/2$, and $\pi$).

Figure 2:
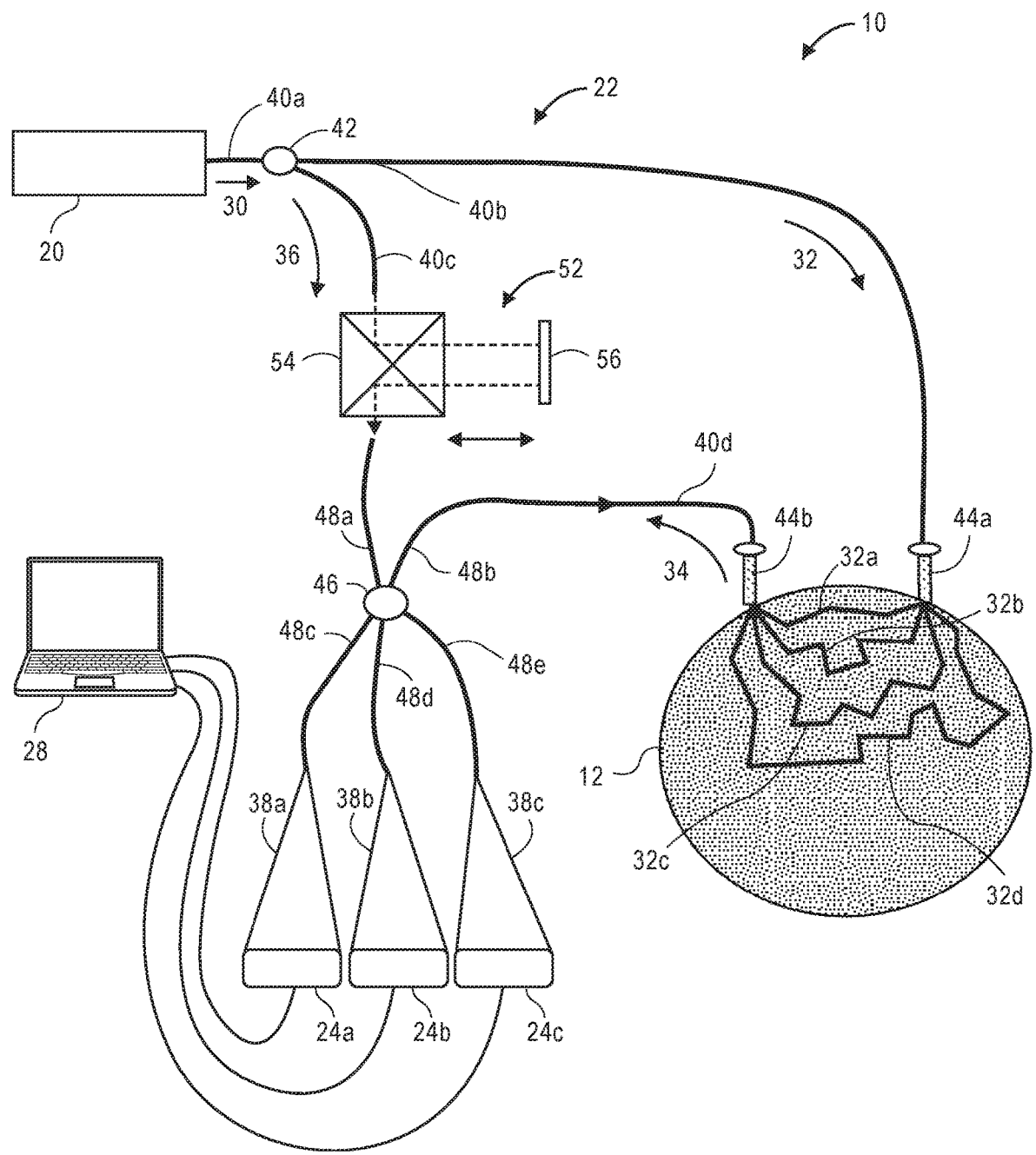
FIG. 2 is a view of a detailed embodiment of the optical measurement system of FIG. 1.

Referring to FIG. 2, a more detailed implementation of the interferometer 22 will now be described. In this implementation, the interferometer 22 is optical fiber-based (i.e., uses optical fibers to direct light between the components), although in alternative embodiments, the interferometer 22 may direct light via free-space propagation between the components using optics, such as mirrors, as further illustrated in U.S. Provisional Patent Application Ser. No. 62/637,703, entitled "Ultrasound Modulating Optical Tomography Using Reduced Laser Pulsed Duration," U.S. patent application Ser. No. 16/266,818, entitled "Ultrasound Modulating Optical Tomography Using Reduced Laser Pulsed Duration," U.S. Provisional Patent Application Ser. No. 62/657,634, entitled "Balanced Holography Technique for Imaging in Highly Scattering Medium," U.S. patent application Ser. No. 16/299,067, entitled "Non-Invasive Optical Detection Systems and Methods in Highly Scattering Medium," U.S. Provisional Patent Application Ser. No. 62/667,770, entitled "Ultrasound-Mediated Optical Detection," and U.S. patent application Ser. No. 16/382,461, entitled "Non-Invasive Optical Detection System and Method," which are expressly incorporated herein by reference.

The interferometer 22 comprises an input optical fiber 40a that optically couples the interferometer 22 to the optical source 20 for receiving the source light 30 from the optical source 20; an optical fiber-based optical beam splitter 42 for splitting the source light 30 into the sample light 32 and the reference light 36, and a sample arm optical fiber 40b and a reference arm optical fiber 40c for respectively propagating the sample light 32 and reference light 36 along the sample arm and reference arm of the interferometer 22.

The optical beam splitter 42 may not necessarily split the source light 30 equally into the sample light 32 and reference light 36, and it may actually be more beneficial for the optical beam splitter 42 to split the source light 30 unevenly, such that the intensity of the sample light 32 is higher than the intensity of the reference light 36 (e.g., 99/1 power ratio), since much of the sample light 32 will be lost after passing through the brain 12. That is, the intensity of the sample light 32 should be boosted relative to the reference light 36 to compensate for the losses incurred by the sample light 32 as it passes through the brain 12 and the fact that only a small portion of neural-encoded signal light 34 (described below) exiting the brain 12 will be detected.

The sample arm optical fiber 40b delivers the sample light 32 via an output port 44a into the brain 12, such that the sample light 32 scatters diffusively through the brain 12, and back out again, exiting as the neural-encoded signal light 34. As it scatters diffusively through the brain 12, various portions of the sample light 32 will take different paths through the brain 12. For purposes of brevity, only four sample light portions 32a-32d are illustrated as traveling along optical paths of different lengths (from shallow to deeper areas of the brain 12), which are all combined into the exiting neural-encoded signal light 34, although it should be appreciated that the diffused sample light 32 will travel along many more optical paths through the brain 12. The interferometer 22 further comprises an output optical fiber 40d configured for receiving the neural-encoded signal light 34 from the brain 12 via an input port 44b.

The interferometer 22 comprises an optical beam combiner 46 configured for receiving the neural-encoded signal light 34 from the output optical fiber 40d, receiving the reference light 36 from the reference arm optical fiber 40c, and combining the neural-encoded signal light 34 and reference light 36 via superposition to generate the three-phase modulated interference light patterns 38a, 38b, and 38c. In the illustrated embodiment, the optical beam combiner 46 is an optical fiber-based optical beam combiner comprising first input 48a configured for receiving the reference light 36, a second input 48b configured for receiving the neural-encoded signal light 34, a first output 48c configured for outputting the first phase-modulated interference light pattern 38a to the first optical detector 24a, a second output 48d configured for outputting the second phase-modulated interference light pattern 38b to the second optical detector 24b, and a third output 48e configured for outputting the third phase-modulated interference light pattern 38c to the third optical detector 24c. In the illustrated embodiment, the optical beam combiner 46 takes the form of a 3×3 fiber coupler with one unused input port. Thus, optical beam combiner 46 combines the neural-encoded signal light 34 and the reference light 36 into an interference light pattern 38, and splits the interference light pattern 38 into the three phase-modulated interference light patterns 38a, 38b, 38c. Due to power conservation, a six-port network, such as the optical beam combiner 46, inherently outputs phase-modulated interference light patterns 38 that are ninety degrees out of phase from each other. In an alternative embodiment, multiple free-space optical beam combiners can be used to generate the three interference light patterns 38a, 38b, 38c, e.g., as described in U.S. Provisional Patent Application Ser. No. 62/637,703, entitled "Ultrasound Modulating Optical Tomography Using Reduced Laser Pulsed Duration," and U.S. patent application Ser. No. 16/266,818, entitled "Ultrasound Modulating Optical Tomography Using Reduced Laser Pulsed Duration," which are expressly incorporated herein by reference.

The interferometer 22 further comprises a path length adjustment mechanism 52 configured for adjusting the optical path length of the reference arm to nominally match the expected optical path length of the sample arm. Those skilled in the art will recognize that the reference arm and sample arm (not shown) are integrated and different arms of the interferometer 22. The path length adjustment mechanism 52 may include control inputs (not shown) for receiving control signals from the controller 26 to cause the path length adjustment mechanism 52 to adjust the optical path length of the reference arm. The path length adjustment mechanism 52 includes an optical beam splitter/combiner 54 and an adjustable mirror 56 that can be displaced relative to the optical beam splitter/combiner 54. The beam/splitter combiner 54 is configured for redirecting the reference light 36 at a ninety-degree angle towards the mirror 56, and redirecting the reference light 36 reflected back from the mirror 56 at a ninety-degree angle towards the optical beam splitter/combiner 54. Thus, adjusting the distance between the mirror 56 and the optical splitter/combiner 54 will adjust the optical path length of the reference arm to match the optical path length of the sample arm.

Figure 3:
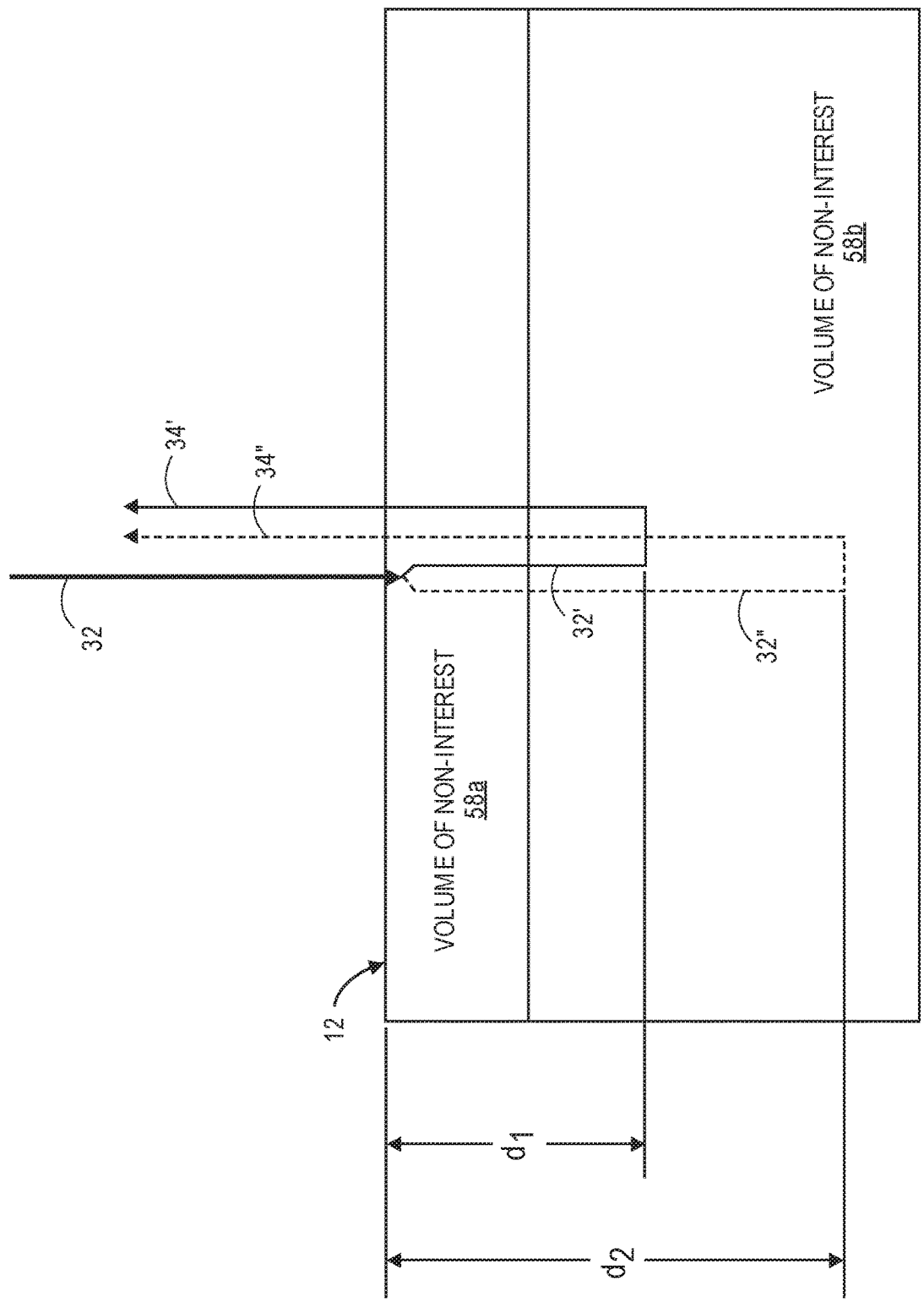
FIG. 3 is diagram illustrating an exemplary path-length selection technique employed by the optical measurement system of FIG. 1.

Referring now to FIG. 3, the path length adjustment mechanism 52 may be adjusted to select the path length of the sample light 32 through a volume of non-interest 58a (e.g., skin, scalp, and skull) and into a volume of interest 58b (e.g., brain). In particular, the optical measurement system 10 uses path-length selection to distinguish between a first sample light portion 32' and a second sample light portion 32", the first sample light portion 32' having a first optical path length being backscattered by the volume of interest 58b at a depth $d_1$ as signal light 34', and thus encoded with the optical parameters of the volume of interest 58b at that depth $d_1$, and the second sample light portion 32" having a second optical path length different from the first optical path length and being backscattered by the volume of interest 58b at a depth $d_2$ as signal light 34", and thus encoded with the optical parameters of the volume of interest 58b at that depth $d_2$. Thus, different depths of the volume of interest 58b may be selectively targeted for measurement by the optical measurement system 10.

That is, the path length adjustment mechanism 52 can be adjusted, such that the optical path length of the first sample light portion 32' (in contrast to the optical path length of the second sample light portion 32") matches the optical path length of the reference light 36 within the optical coherence length of the source light 30, such that only the signal light 34', resulting from the first sample light portion 32' that is backscattered by volume of interest 58b and contributes to the interference light patterns 38a, 38b, 38c. Similarity, the path length adjustment mechanism 52 can be adjusted, such that the optical path length of the second sample light portion 32" (in contrast to the optical path length of the first sample light portion 32') matches the optical path length of the reference light 36 within the optical coherence length of the source light 30, such that only the signal light 34", resulting from the second sample light portion 32" that is backscattered by volume of interest 58b and contributes to the interference light patterns 38a, 38b, 38c. Further details describing coherence gating systems are set forth in U.S. patent application Ser. No. 15/853,538, entitled "Systems and Methods for Quasi-Ballistic Photon Optical Coherence Tomography in Diffusive Scattering Media Using a Lock-In Camera Detection" (now U.S. Pat. No. 10,219,700), which is expressly incorporated herein by reference.

Referring back to FIG. 1, the optical detectors 24a, 24b, and 24c are configured for respectively detecting the three phase-modulated interference light patterns 38a, 38b, 38c and respectively outputting absolute intensity values over the measurement period. The measurement period may be any suitable period that results in the desired signal-to-noise-ratio (SNR), e.g., at least 50 µs, and preferably at least 100 µs. Notwithstanding this, it is desired that the measurement period be as short as possible within the constraints of sufficient SNR. Each of the optical detectors 24a, 24b, 24c includes control inputs (not shown) for receiving control signals from the controller 26, such that detection of the intensity values can be coordinated with the delivery of the sample light 32.

Each of the optical detectors 24a, 24b, 24c may comprise a single photodiode, e.g., a photodiode (PD), an avalanche photodiode (AVD), or a single photon avalanche diode (SPAD), although pixel arrays (as in a camera or photodiode array) or form a sub-pixel array of a single pixel array may be used. Because the full distributed photon time-of-flight (DTOF) of the neural-encoded signal light 34 need not be measured, each of the optical detectors 24a, 24b, and 24c may be conventional and may be operated at a relatively low speed, e.g., 1 MHz. The three optical detectors 24a, 24b, 24c may be a completely integrated device or may be arranged on closely spaced multiple devices or device regions.

The processor 28, which may take the form of a general purpose computer, shown in FIG. 2, configured for determining a time-lapsed complex field of the neural-encoded signal light 34 over the measurement period based on the detected phase-modulated interference light patterns 38a, 38b, 38c, performing an autocorrelation function of the time-lapsed complex field of the neural-encoded signal light 34 to determine a decorrelation speed of the neural-encoded signal light 34, and identifying a physiological event (in this case, a fast-optical signal, and optionally an additional hemodynamic change) in the brain 12 based on the determined decorrelation speed of the neural-encoded signal light 34.

The processor 28 may determine the time-lapsed complex field of the neural-encoded signal light 34 in accordance with the following equations:

$$I_1 = (E_s + E_r)^2 = |E_s|^2 + |E_r|^2 + 2|E_s||E_r|\cos(\theta); \quad [1]$$

$$I_2 = (E_s + E_r e^{-(\pi/2)})^2 = |E_s|^2 + |E_r|^2 + 2|E_s||E_r|\cos(\theta - \pi/2) = 2|E_s||E_r|\sin(\theta); \text{ and} \quad [2]$$

$$I_3 = (E_s + E_r e^{-(\pi)})^2 = |E_s|^2 + |E_r|2 - 2|E_s||E_r|\cos(\theta), \quad [3]$$

where $I_1$ is the current on detector 1 (detector 24a), $I_2$ is the current on detector 2 (detector 24b), $I_3$ is the current on detector 3 (detector 24c), $E_s$ is the intensity of the neural-encoded signal light 34, $E_r$ is the intensity of the reference light 36, and 8 is the phase of the optical field, which reflects the instantaneous phase of the neural-encoded signal light 34. The complex field of $E_s$ (i.e., the real part ($E_s$*cos θ) and the imaginary part ($E_s$*sin θ)) can be determined from equations [1]-[3] as:

$$E_s = (I_1 - I_3) + i(I_2 - (I_1 + I_3)/2) \quad [4]$$

Figure 4A:
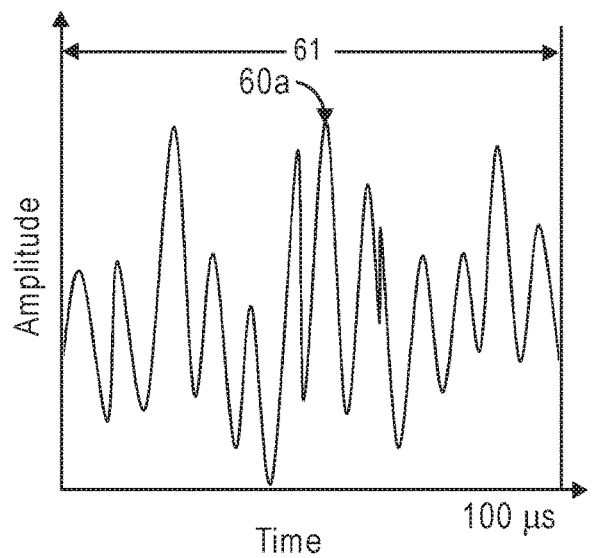
FIG. 4A is a timing diagram of an exemplary amplitude of physiological-encoded signal light resulting in the delivery of sample light into an anatomical structure by the optical measurement system of FIG. 1.
Figure 4B:
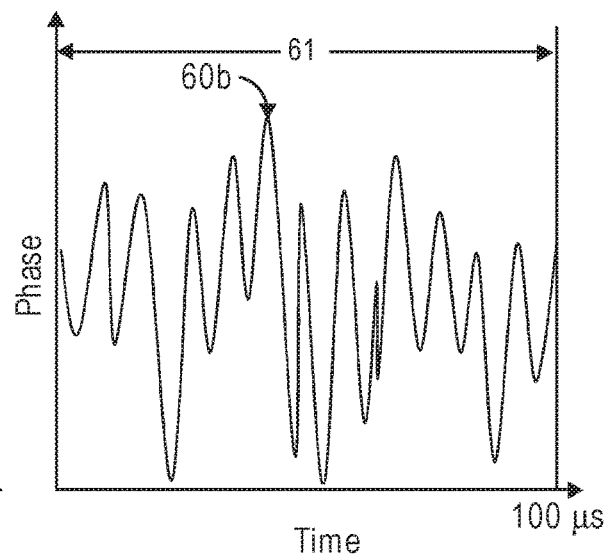
FIG. 4B is a timing diagram of an exemplary phase of physiological-encoded signal light resulting in the delivery of sample light into an anatomical structure by the optical measurement system of FIG. 1.
Figure 4C:
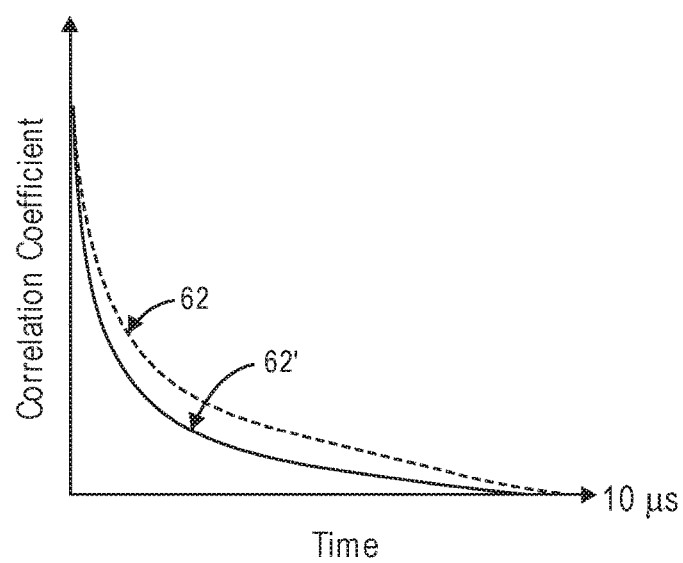
FIG. 4C is a timing diagram of exemplary decorrelation speeds of the physiological-encoded signal light resulting in the delivery of sample light into an anatomical structure by the optical measurement system of FIG. 1.

One exemplary time-lapsed complex field of the neural-encoded signal light 34 in terms of intensity 60a and phase 60b is respectively plotted over a measurement period 61 of 100 μs, as illustrated in FIGS. 4A and 4B. As time lapses, the amplitude and phase of the neural-encoded signal light 34 fluctuates. The quicker the complex field of the neural-encoded signal light 34 fluctuates, the faster the signal light 34 decorrelates, and it is this decorrelation that the processor 28 measures in terms of decorrelation speed (i.e., the magnitude of decorrelation as a function of time). As illustrated in FIG. 4C, the decorrelation speed 62 indicates that the time-lapsed complex field of the neural-encoded signal light 34 decorrelates at an exponential rate, such that maximum correlation occurs at time=0, and complete decorrelation occurs at approximately time=10 μs.

In the illustrated embodiment, the processor 28 determines the decorrelation speed 62 of the time-lapsed complex field of the neural-encoded signal light 34 by performing an autocorrelation function on the time-lapsed complex field of the neural-encoded signal light 34. In particular, the processor 28 is configured for computing an amplitude of a Fourier transform of the time-lapsed complex field of the physiological-encoded signal light, squaring the amplitude of the Fourier transform of the time-lapsed complex field of the physiological-encoded signal light, and computing an inverse Fourier transform of the squared amplitude of the Fourier transform of the time-lapsed complex field of the neural-encoded signal light 34 to obtain the decorrelation speed 62 of the time-lapsed complex field of the neural-encoded signal light 34 (as exemplified in FIG. 4C).

Once the processor 28 obtains the decorrelation speed 62 of the time-lapsed complex field of the neural-encoded signal light 34, the processor 28 identifies the fast-optical signal in the brain 12, at least partially, by comparing this determined decorrelation speed 62 of the complex field of the neural-encoded signal light 34 to a reference decorrelation speed. In one embodiment, the processor 28 identifies the fast-optical signal, and thus the neural activity, at the depth in the brain 12 (selected by the coherence length of the source light 30), e.g., by comparing the current decorrelation speed 62 of the complex field of the neural-encoded signal light 34 with a predetermined baseline decorrelation speed or a user-specific baseline decorrelation speed 62' (e.g., a previously determined decorrelation speed of the complex field of the neural-encoded signal light 34, as illustrated in FIG. 4C. It can be appreciated that a fast-optical signal that occurs at the gated depth in the brain 12 of a user will increase the scattering of the neural-encoded signal light 34 at that depth, thereby increasing the decorrelation speed of the neural-encoded signal light 34. Thus, a measurable change exists between the decorrelation speed 62 of the complex field of the neural-encoded signal light 34 in the presence of a fast-optical signal and the decorrelation speed 62' of the complex field of the neural-encoded signal light 34 in the absence of a fast-optical signal, as illustrated in FIG. 4C.

Figure 5B:
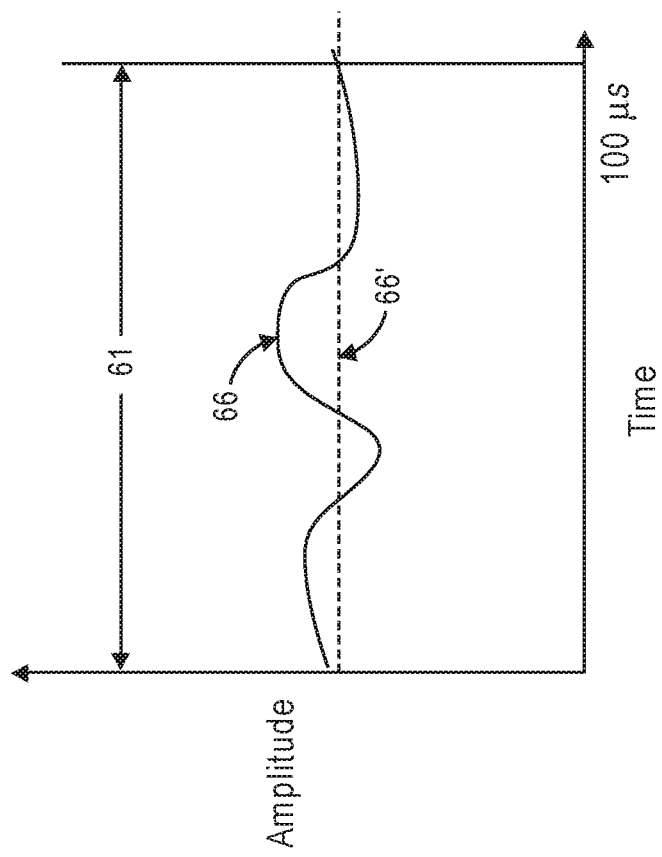
FIG. 5B is a timing diagram of an exemplary moving average of the absolute intensity of the physiological-encoded signal light illustrated in FIG. 5A.
Figure 5A:
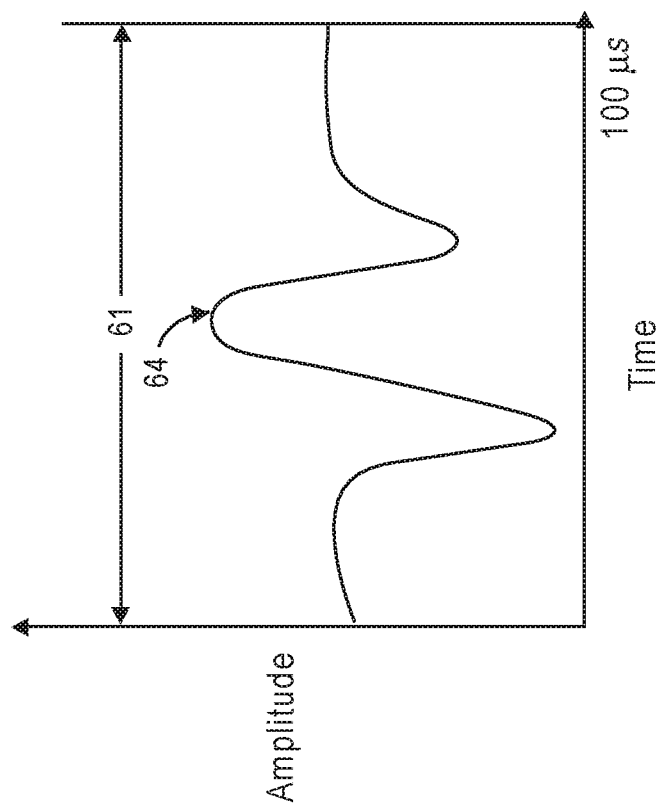
FIG. 5A is a timing diagram of an exemplary absolute intensity of physiological-encoded signal light resulting in the delivery of sample light into an anatomical structure by the optical measurement system of FIG. 1.

Referring now to FIGS. 5A and 5B, the curve shown in FIG. 5A represents a time-lapsed absolute intensity 64 of the neural-encoded signal light 34 (shown in FIG. 1). The curve shown in FIG. 5B represents the computed moving average 66 of the time-lapsed absolute intensity 64, and the dashed line straight curve represents a baseline absolute intensity 66' of the neural-encoded signal light 34. Given the defined terms for the represented curves shown in FIGS. 5A and 5B, the processor 28 is optionally configured for; (a) determining a time-lapsed absolute intensity 64 of the neural-encoded signal light 34 over the measurement period 61 of 100 μs based on the three detected phase-modulated interference light patterns 38a, 38b, 38c (e.g., by computing the average of their absolute intensities or simply using one of their absolute intensities), as illustrated in FIG. 5A, (b) computing a moving average 66 of the time-lapsed absolute intensity 64 of the physiological-encoded signal light using a suitable time window (e.g., 10 μs) over the measurement period 61, as illustrated in FIG. 5B, and (c) identifying another physiological event (in this case, a hemodynamic change) in the brain 12 based on the computed moving average 66 of the time-lapsed absolute intensity 64 of the neural-encoded signal light 34 over the measurement period 61. It can be appreciated that a hemodynamic change that occurs at the gated depth in the brain 12 will change the absorption of the neural-encoded signal light 34 at that depth, thereby modifying the time-lapsed absolute intensity 64 of the neural-encoded signal light 34 over the measurement period. Thus, a measurable change exists between the computed moving average 66 of the time-lapsed absolute intensity 64 of the neural-encoded signal light 34 in the presence of a fast-optical signal and a baseline absolute intensity 66' of the neural-encoded signal light 34 in the absence of a fast-optical signal, as illustrated in FIG. 5B. Thus, the processor 28 identifies the hemodynamic change in the brain 12, at least partially, by measuring the fluctuation of the computed moving average 66 of the time-based absolute intensity 64 of the neural-encoded signal light 34 over the measurement period 61.

Figure 6:
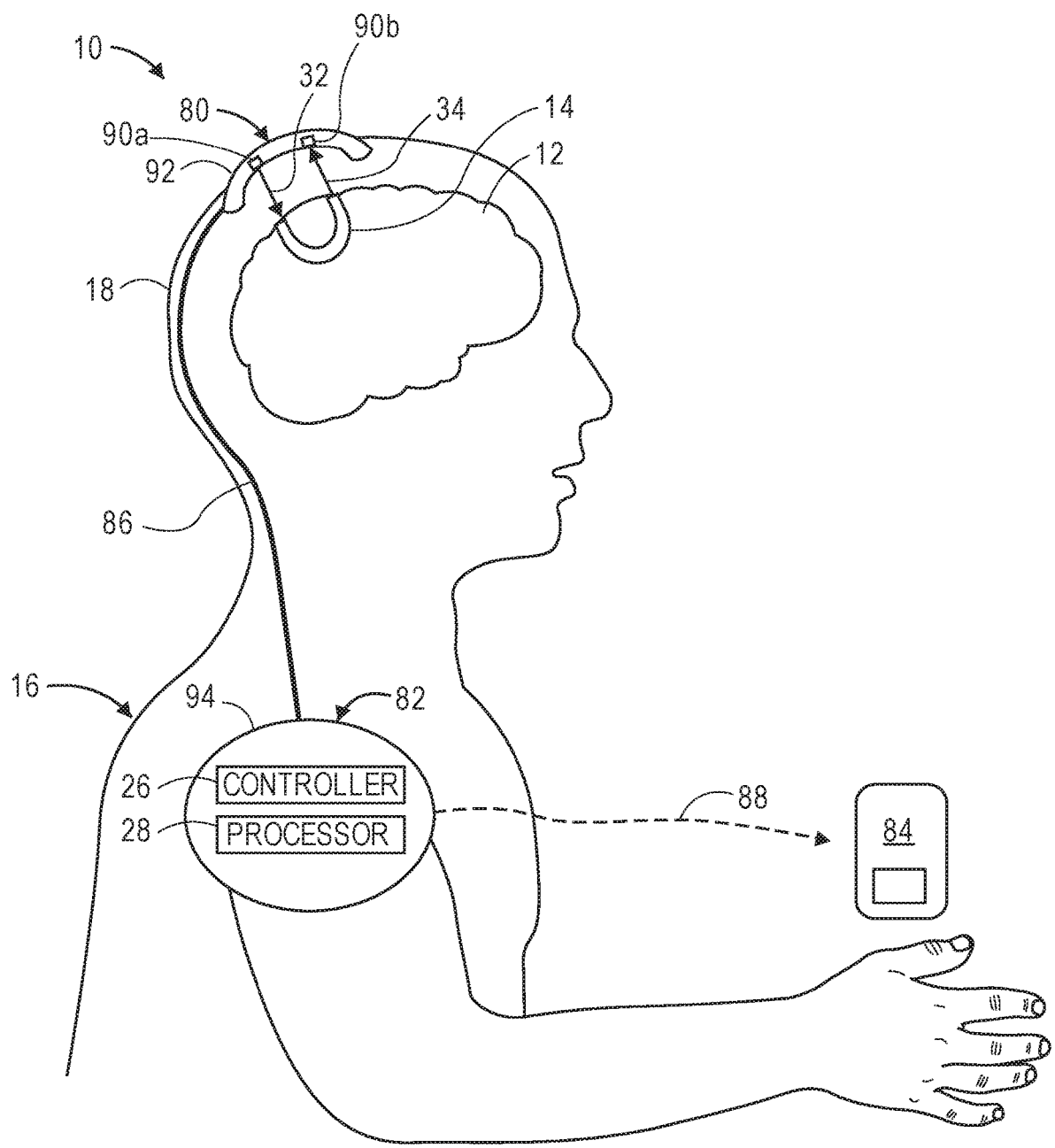
FIG. 6 is a view of physical implementation of the optical measurement system of FIG. 1.

Referring now to FIG. 6, the physical implementation of the optical measurement system 10 for use in localizing a fast-optical signal in the brain 12 of a user 16 will be described. The optical measurement system 10 includes a wearable unit 80 that is configured for being applied to the user 16, and in this case, worn on the head 18 of the user 16; an auxiliary head-worn or non-head-worn unit 82 (e.g., worn on the neck, shoulders, chest, or arm) coupled to the wearable unit 80 via a wired connection 86 (e.g., electrical wires); and an optional remote processor 84 in communication with the patient-wearable auxiliary unit 82 coupled via a wired connection 88 (e.g., electrical wires). Alternatively, the optical measurement system 10 may use a non-wired connection (e.g., wireless radio frequency (RF) signals (e.g., Bluetooth, Wifi, cellular, etc.) or optical links (e.g., fiber optic or infrared (IR)) for providing power to or communicating between the respective wearable unit 80 and the auxiliary unit 82, and/or a wired connection between the auxiliary unit 82 and the remote processor 84.

The wearable unit 80 comprises the optical source 20, interferometer 22, and optical detectors 24 (illustrated in FIGS. 1 and 2), an output port 90*a* for emitting the sample light 32 generated by the optical source 20 (illustrated in FIGS. 1 and 2) into the head 18 of the user 16, an input port 90*b* configured for receiving the neural-encoded signal light 34 from the head 18 of the user 16 and delivering it to the interferometer 22, and ultimately the optical detectors 24 (illustrated in FIGS. 1 and 2), and a support housing structure 92 containing the optical source 20, interferometer 22, optical detectors 24, and ports 90*a*, 90*b*.

The auxiliary unit 82 comprises the controller 26 and the processor 28 (illustrated in FIGS. 1 and 2), at least a portion (e.g., any analog portion) of the processor 28 may alternatively be located in the wearable unit 80. The auxiliary unit 82 further comprises a housing 94 containing the controller 26 and processor 28. The controller 26 is configured for controlling the operational functions of the wearable unit 80, whereas the processor 28 is configured for processing the neural-encoded signal light 34 acquired by the wearable unit 80 to localize the fast-optical signal within the brain 12. The auxiliary unit 82 may additionally include a power supply (which if head-worn, may take the form of a rechargeable or non-chargeable battery), a control panel with input/output functions, a display, and memory. Alternatively, power may be provided to the auxiliary unit 82 wirelessly (e.g., by induction). The remote processor 84 may store data from previous sessions, and include a display screen.

Figure 7:
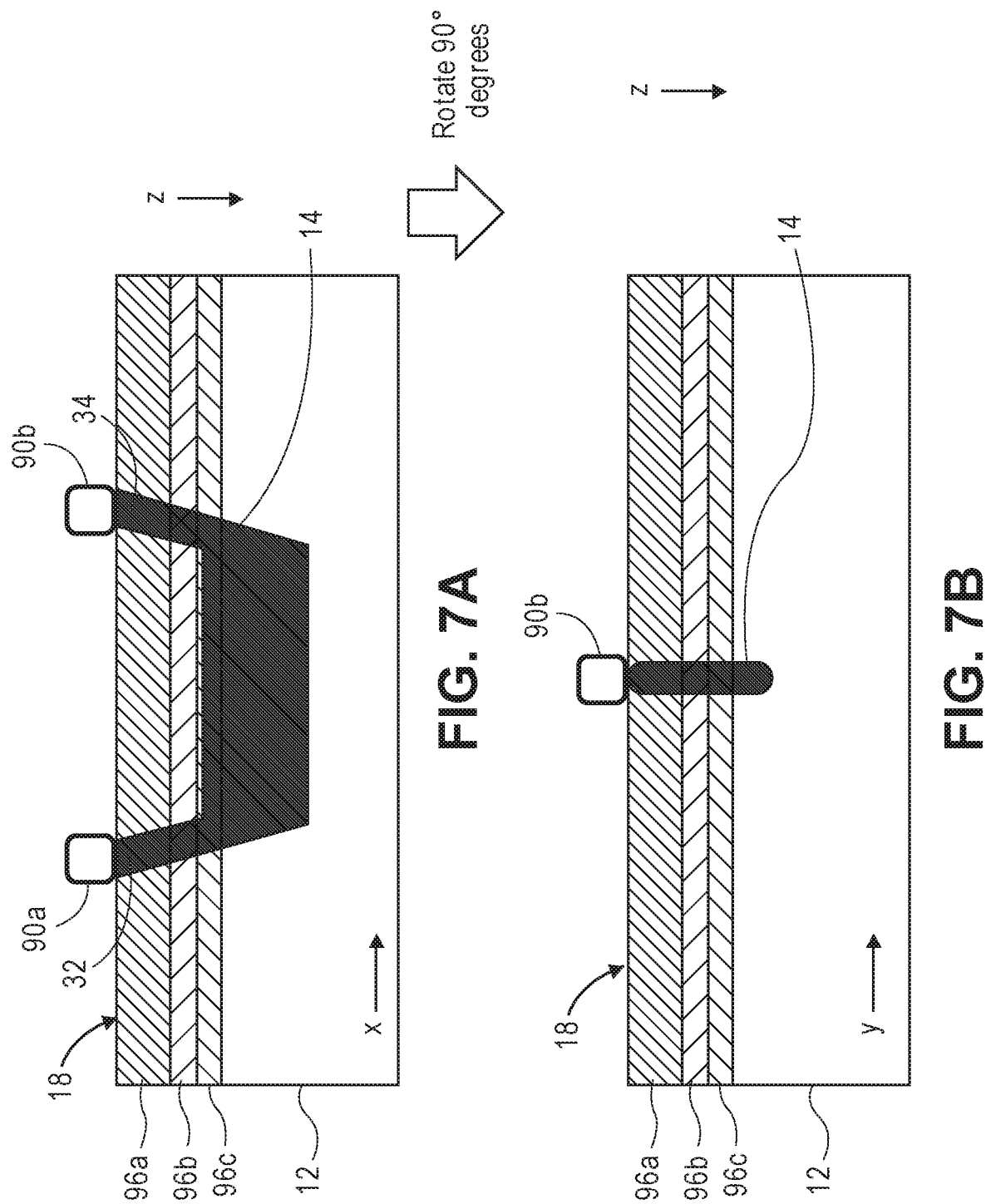
FIG. 7A is one profile view of one arrangement of the output port and input port of the wearable unit of FIG. 6, particularly illustrating the creation of a sample path in the head between the ports.
FIG. 7B is another profile view of the arrangement of the output port and input port of the wearable unit of FIG. 6.

As better illustrated in FIGS. 7A and 7B, the wearable unit 80 is configured for emitting the sample light 32 into the brain 12 via the output port 90*a*, where is scatters, resulting in the neural-encoded signal light 34 that exits the brain 12, and is received by the input port 90*b* of the wearable unit 80. In particular, the sample light 32 first passes through the scalp 96*a*, skull 96*b*, and cerebral spinal fluid (CSF) 96*c* along a relatively straight path, enters the brain 12, then exits in reverse fashion along a relatively straight path through the CSF 96*c*, skull 96*b*, and scalp 96*a*, thereby defining a banana-shaped sample path 14. The wearable unit 80 may alternatively, by adding additional optical source-detector pairs, create multiple spatially separated optical paths 14 along which the light may propagate to enable x-y spatial localization of the fast-optical signal.

Referring back to FIG. 6, the support housing structure 92 may be shaped, e.g., have a banana, headband, cap, helmet, beanie, other hat shape, or other shape adjustable and conformable to the user's head (brain 12), such that the ports 90*a*, 90*b* are in close contact with the outer skin of the head 18, and in this case, the scalp of the user 16. In an alternative embodiment, optical fibers (not shown) may be respectively extended from the ports 90*a*, 90*b*, thereby freeing up the requirement that the ports 90*a*, 90*b* be disposed in close proximity to the surface of the head 18. In any event, an index matching fluid may be used to reduce reflection of the light generated by the wearable unit 80 from the outer skin of the scalp. An adhesive or belt (not shown) can be used to secure the support housing structure 92 to the head 18 of the user 16.

Figure 8:
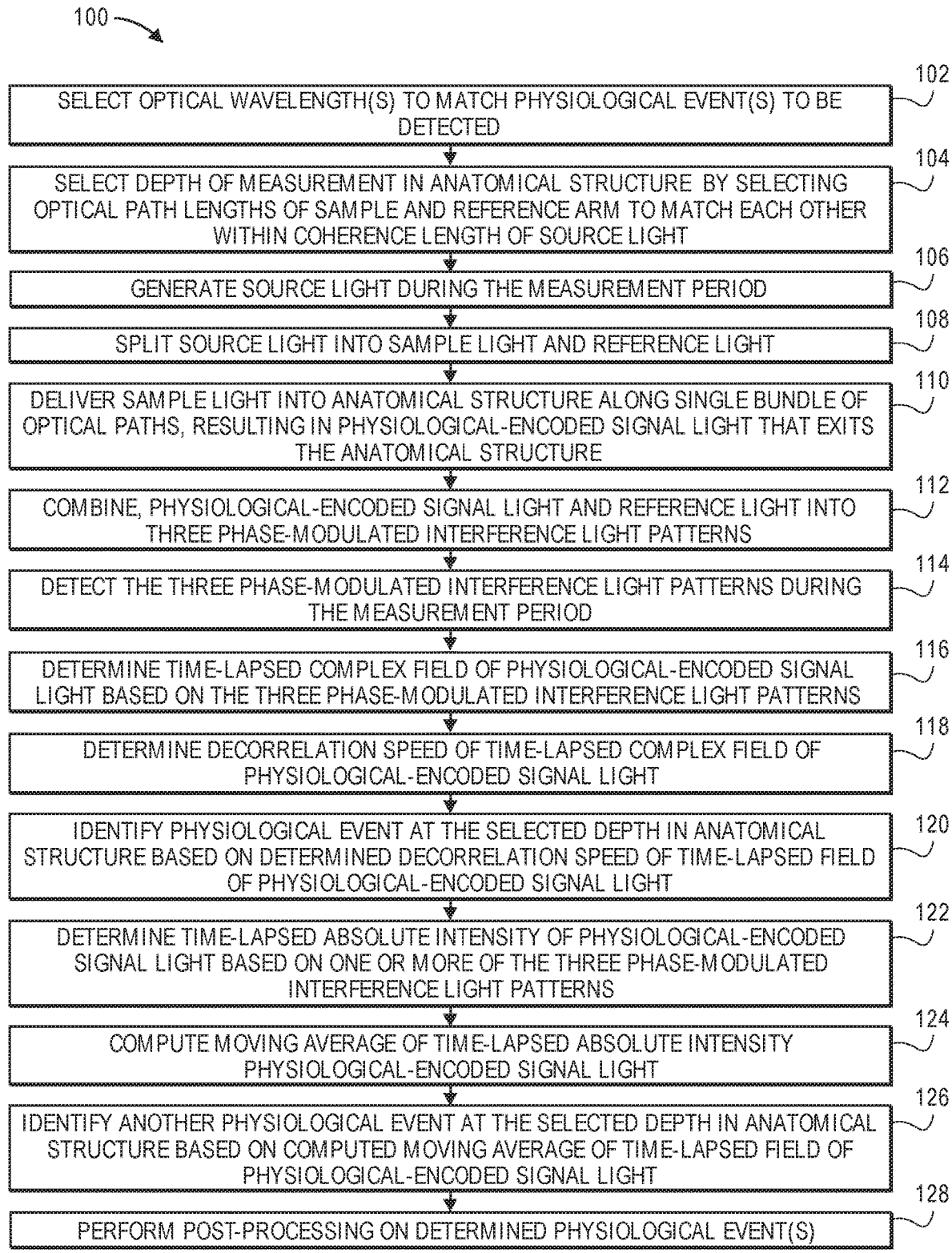
FIG. 8 is a flow diagram illustrating one method used by the optical measurement systems of FIG. 1 to non-invasively detect one or more physiological events within an anatomical structure.

Referring to FIG. 8, having described the structure and function of the optical measurement system 10, one particular method 100 performed by the optical measurement system 10 to non-invasively determine the depth of a physiological event (in this case, a fast-optical signal) in the anatomical structure (in this case, the brain 12) will now be described.

First, the optical wavelength(s) of the source light 30 is selected to match the physiological event(s) to be detected in the brain 12 (step 102). In this case, the physiological event is a fast-optical signal, and thus, one optical wavelength may be greater than 850 nm. In the case where it is desirable to additionally detect blood oxygen concentration, another optical wavelength may be selected to be in the range of 650 nm to 750 nm. Next, the controller 26 adjusts interferometer 22, such that the optical path lengths of the sample arm and reference arm of the interferometer 22 match each other within a coherence length of the source light 30 to detect optical parameters at the desired depth in the anatomical structure (in this case, the brain 12), e.g., by sending a control signal to the path length adjustment mechanism 52, as shown in FIG. 2 (step 104).

Then, the controller 26 operates the optical source 20 to generate source light 30 during the measurement period, e.g., by sending a control signal to the drive circuit associated with the optical source 20 (step 106). For example, the source light 30 may be a continuous wave (CW) source light, although in alternative embodiments, the optical source 20 may be a pulsed wave (PW) source light, in which case, the pulse width of the source light 30 can be at least as long as the measurement period. The interferometer 22 (e.g., via the optical beam splitter 42) splits the source light 30 into sample light 32 and reference light 36 (step 108), delivers the sample light 32 into the anatomical structure 12 (in this case, the brain) along a single bundle of optical paths 14, such that the sample light 32 is scattered by the brain 12, resulting in physiological-encoded (in this case, neural-encoded) signal light 34 that exits the brain 12 (step 110), and combines, the neural-encoded signal light 34 and the reference light 36 into three phase-modulated interference light patterns 38*a*, 38*b*, 38*c* (step 112).

Next, the optical detectors 24*a*, 24*b*, 24*c* respectively detecting the three phase-modulated interference light patterns 38*a*, 38*b*, 38*c* during the measurement period (step 114), and the processor 28 determines a time-lapsed complex field of the neural-encoded signal light 34 based on the three detected phase-modulated interference light patterns 38*a*, 38*b*, 38*c* (e.g., using equation [4]) (step 116), determines a decorrelation speed 62 of the time-lapsed complex field of the neural-encoded signal light 34 (e.g., by performing an autocorrelation function on the time-lapsed complex field of the neural-encoded signal light 34) (step 118), and identifies a physiological event (in this case, a fast-optical signal) at the selected depth in the brain 12 based on the determined decorrelation speed 62 of the neural-encoded signal light 34 in the manner described above with respect to FIG. 4A-4C, e.g., by comparing the decorrelation speed 62 of the time-lapsed complex field of the neural-encoded signal light 34 to a baseline decorrelation speed 62' (step 120).

The processor 28 optionally determines a time-lapsed absolute intensity 64 of the neural-encoded signal light 34 over the measurement period based one or more the three detected phase-modulated interference light patterns 38*a*, 38*b*, 38*c* (e.g., computing the average or using only one or more of the three phase modulated interference light patterns 38*a*, 38*b*, 38*c*) (step 122), computes a moving average 66 of the time-lapsed absolute intensity 64 of the neural-encoded signal light 34 over the measurement period (step 124), and identifies another physiological event (in this case, a hemodynamic change) at the selected depth in the brain 12 based on the computed moving average 66 of the time-lapsed absolute intensity 64 of the neural-encoded signal light 34 over the measurement period in the manner described above with respect to FIG. 5A-5B, e.g., by comparing the computed moving average 66 of the time-lapsed complex field of the neural-encoded signal light 34 to the baseline absolute intensity 66' of the neural-encoded signal light 34 (step 126).

In the case where multiple bundles of optical paths 14 through the brain 12 are created using other source-detector arrangements (e.g., single-source multi-detector, multi-source single-detector, or multi-source multi-detector) to simultaneously create multiple sample paths 14 spatially separated from each other within the brain 12 in a single measurement period, or by using a movable source-detector arrangement, the processor 28 may also localize the fast-optical signal and hemodynamic change in an x-y plane along the surface of the brain 12, such that a three-dimensional location of the fast-optical signal within the brain 12 is determined. The processor 28 may then perform post-processing on the determined fast-optical signal and optional hemodynamic change, e.g., determining the presence and location of neural activity within the brain 12 (step 128).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A non-invasive optical measurement system, comprising:
   an optical source configured for generating a source light during a measurement period;
   an interferometer configured for splitting the source light into sample light and reference light, delivering the sample light into an anatomical structure, such that the sample light is scattered by the anatomical structure, resulting in physiological-encoded signal light that exits the anatomical structure, and combining the physiological-encoded signal light and the reference light into at least three phase-modulated interference light patterns, an optical path length of the respective source light and an optical path length of the sample light matching within a coherence length of the source light;
   at least three optical detectors configured for respectively detecting the at least three phase-modulated interference light patterns over the measurement period; and
   a processor configured for determining a time-lapsed complex field of the physiological-encoded signal light over the measurement period based on a combination of the at least three detected phase-modulated interference light patterns, determining a decorrelation speed of the time-lapsed complex field of the physiological-encoded signal light, and identifying a physiological event in the anatomical structure based on the determined decorrelation speed of the physiological-encoded signal light.

2. The non-invasive optical measurement system of claim 1, wherein the anatomical structure is a brain.

3. The non-invasive optical measurement system of claim 2, wherein the physiological event is indicative of neural activity.

4. The non-invasive optical measurement system of claim 3, wherein the physiological event is a fast-optical signal.

5. The non-invasive optical measurement system of claim 1, wherein the measurement period is at least 50 μs.

6. The non-invasive optical measurement system of claim 1, wherein the measurement period is at least 100 μs.

7. The non-invasive optical measurement system of claim 1, wherein the at least three phase-modulated interference light patterns are ninety degrees out of phase.

8. The non-invasive optical measurement system of claim 1, wherein the interferometer comprises a beam splitter configured for splitting the source light into the sample light and the reference light, and an optical beam combiner configured for combining the physiological-encoded signal light and the reference light into the at least three phase-modulated interference light patterns.

9. The non-invasive optical measurement system of claim 8, wherein the optical beam combiner comprises a first input port configured for receiving the physiological-encoded signal light, a second input port configured for receiving the reference light, a first output port configured for outputting a first one of the at least three phase-modulated interference light patterns to a first one of the three optical detectors, a second output port configured for outputting a second one of the at least three phase-modulated interference light patterns to a second one of the three optical detectors, and a third output port configured for outputting a third one of the at least three phase-modulated interference light patterns to a third one of the three optical detectors.

10. The non-invasive optical measurement system of claim 1, wherein the processor is configured for determining the decorrelation speed of the time-lapsed complex field of the physiological-encoded signal light by performing an autocorrelation function of the time-lapsed complex field of the physiological-encoded signal light.

11. The non-invasive optical measurement system of claim 10, wherein the processor is configured for performing the autocorrelation function of the time-lapsed complex field of the physiological-encoded signal light by computing an amplitude of a Fourier transform of the time-lapsed complex field of the physiological-encoded signal light, squaring the amplitude of the Fourier transform of the time-lapsed complex field of the physiological-encoded signal light, and computing an inverse Fourier transform of the squared amplitude of the Fourier transform of the time-lapsed complex field of the physiological-encoded signal light.

12. The non-invasive optical measurement system of claim 1, wherein the processor is configured for identifying the physiological event in the anatomical structure, at least partially, by comparing the determined decorrelation speed of the physiological-encoded signal light to a reference decorrelation speed.

13. The non-invasive optical measurement system of claim 1, wherein the processor is configured for determining a time-lapsed absolute intensity of the physiological-encoded signal light over the measurement period based on the at least three detected phase-modulated interference light patterns, computing a moving average of the time-lapsed absolute intensity of the physiological-encoded signal light over the measurement period, and identifying another physiological event in the anatomical structure based on the computed moving average of the time-lapsed absolute intensity of the physiological-encoded signal light over the measurement period.

14. The non-invasive optical measurement system of claim 13, wherein the other physiological event is a hemodynamic change.

15. The non-invasive optical measurement system of claim 1, wherein the optical source comprises a coherence length equal to or less than 1 cm.

16. The non-invasive optical measurement system of claim 1, wherein the optical source is a continuous wave (CW) optical source.

17. A non-invasive optical measurement method, comprising:
generating source light during a measurement period;
splitting the source light into sample light and reference light;
delivering the sample light into an anatomical structure, such that the sample light is scattered by the anatomical structure, resulting in physiological-encoded signal light that exits the anatomical structure;
combining the physiological-encoded signal light and the reference light into at least three phase-modulated interference light patterns, an optical path length of the source light and an optical path length of the sample light matching within a coherence length of the source light;
respectively detecting the at least three phase-modulated interference light patterns over the measurement period;
determining a time-lapsed complex field of the physiological-encoded signal light over the measurement period based on the at least three detected phase-modulated interference light patterns;
determining a decorrelation speed of the time-lapsed complex field of the physiological-encoded signal light; and
identifying a physiological event in the anatomical structure based on the determined decorrelation speed of the physiological-encoded signal light.

18. The non-invasive optical measurement method of claim 17, wherein the anatomical structure is a brain.

19. The non-invasive optical measurement method of claim 17, wherein the physiological event is indicative of neural activity.

20. The non-invasive optical measurement method of claim 19, wherein the physiological event is a fast-optical signal.

21. The non-invasive optical measurement method of claim 17, wherein the measurement period is at least 50 μs.

22. The non-invasive optical measurement method of claim 17, wherein the measurement period is at least 100 μs.

23. The non-invasive optical measurement method of claim 17, wherein the at least three phase-modulated interference light patterns are ninety degrees out of phase.

24. The non-invasive optical measurement method of claim 17, wherein the decorrelation speed of the time-lapsed complex field of the physiological-encoded signal light is determined by performing an autocorrelation function of the time-lapsed complex field of the physiological-encoded signal light.

25. The non-invasive optical measurement method of claim 24, wherein the autocorrelation function of the time-lapsed complex field of the physiological-encoded signal light is performed by computing a Fourier transform of the time-lapsed complex field of the physiological-encoded signal light, squaring the Fourier transform of the time-lapsed complex field of the physiological-encoded signal light, and computing an inverse Fourier transform of the squared Fourier transform of the time-lapsed complex field of the physiological-encoded signal light.

26. The non-invasive optical measurement method of claim 17, wherein the physiological event in the anatomical structure is identified, at least partially, by comparing the determined decorrelation speed of the physiological-encoded signal light to a reference decorrelation speed.

27. The non-invasive optical measurement method of claim 17, further comprising:
determining a time-lapsed absolute intensity of the physiological-encoded signal light over the measurement period based on the at least three detected phase-modulated interference light patterns;
computing a moving average of the time-lapsed absolute intensity of the physiological-encoded signal light over the measurement period; and
identifying another physiological event in the anatomical structure based on the computed moving average of the time-lapsed absolute intensity of the physiological-encoded signal light over the measurement period.

28. The non-invasive optical measurement method of claim 27, wherein the other physiological event is a hemodynamic change.

29. The non-invasive optical measurement method of claim 17, wherein the source light has a coherence length equal to or less than 1 cm.

30. The non-invasive optical measurement method of claim 17, wherein the source light is continuous wave (CW) source light.

* * * * *